(12) United States Patent
Hsu et al.

(10) Patent No.: US 9,724,329 B2
(45) Date of Patent: Aug. 8, 2017

(54) STIMULATING IMMUNE RESPONSE

(75) Inventors: Andy Kang-Wei Hsu, Mitcham (AU); Jake Shortt, Northcote (AU); Paul Neeson, East Ivanhoe (AU); Ricky Wayne Johnstone, Fairfield (AU); David Ritchie, Mont Albert (AU)

(73) Assignee: Peter MacCallum Cancer Institute (AU)

( * ) Notice: Subject to any disclaimer, the term of this patent is extended or adjusted under 35 U.S.C. 154(b) by 159 days.

(21) Appl. No.: 13/806,656

(22) PCT Filed: Jun. 21, 2011

(86) PCT No.: PCT/AU2011/000752
§ 371 (c)(1),
(2), (4) Date: Apr. 4, 2013

(87) PCT Pub. No.: WO2011/160170
PCT Pub. Date: Dec. 29, 2011

(65) Prior Publication Data
US 2013/0302377 A1    Nov. 14, 2013

(30) Foreign Application Priority Data

Jun. 21, 2010    (AU) ............................... 2010902717

(51) Int. Cl.
| | | |
|---|---|---|
| *A01N 43/36* | (2006.01) |
| *A61K 31/40* | (2006.01) |
| *A61K 45/00* | (2006.01) |
| *A61K 47/00* | (2006.01) |
| *A61K 31/4015* | (2006.01) |

(52) U.S. Cl.
CPC ............................... *A61K 31/4015* (2013.01)

(58) Field of Classification Search
CPC ................................................ A61K 31/4015
USPC ....................................... 514/424; 424/278.1
See application file for complete search history.

(56) References Cited

U.S. PATENT DOCUMENTS

| | | | |
|---|---|---|---|
| 4,772,589 A * | 9/1988 | Kaplan et al. | 514/33 |
| 5,049,580 A | 9/1991 | Crouthamel | |
| 6,040,330 A * | 3/2000 | Hausheer et al. | 514/408 |

FOREIGN PATENT DOCUMENTS

| | | |
|---|---|---|
| EP | 2585060 | 12/2013 |
| WO | WO 94/13254 | 6/1994 |
| WO | WO 2008/015539 | 2/2008 |
| WO | WO 2008/132458 | 11/2008 |
| WO | WO 2010/036702 | 4/2010 |
| WO | WO2010036702 A1 * | 4/2010 |
| WO | WO 2011/160170 | 12/2011 |

OTHER PUBLICATIONS

Cruz et al. (Expert Opinion Investig. Drugs, 2002, 11, 12, 1829-36).*
Wolff, Some consideration for prodrug design, Burger's Medicinal Chemistry and Drug Discovery, 5th Edition, vol. I Principles and Practice, pp. 975-977, 1995.*
Banker et al., Prodrugs, Modern Pharmaceutics, Third Edition and Expanded, pp. 451 and 596 (1996).*
Miller et al. (American J of Oncology, 1998, p. 553-556).*
Gura et al. (Science 1997, Nov. 7, 278).*
Johnson et al., (British J. of Cancer 2001, p. 1424-1431).*
MD Anderson Cancer Document (http://www.mdanderson.org/patient-and-cancer-information/ cancer-information/cancer-types/multiple-myeloma/prevention/index.html) 2015.*
Cancer.org document (http://www.cancer.org/cancer/multiplemyeloma/detailedguide/multiple-myeloma-prevention), 2015.*
Multiple Myeloma Research Foundation (http://www.themmrf.org/multiple-myeloma/multiple-myeloma- causes/myeloma-prevention/), 2015.*
Miller et al. Oncogene, 2002, 21, 3496-3506.*
Quach (Leukemia, 2010, 24, 22-32).*
Crawford, et al., "A 12-Month Clinical Study of LA-2585 (45.0 MG): A New 6-Month Subcutaneous Delivery System for Leuprolide Acetate for the Treatment of Prostate Cancer," Journal of Urology, 145(2):533-536 (2006).
International Search Report and Written Opinion, PCT/AU2011/000752, mailing date Aug. 3, 2011. 8 pages.
Kumar, et al., "Thalidomide and Lenalidomide in the Treatment of Multiple Myeloma," European Journal of Cancer, 45(11):1612-1622 (2006).
Li, et al, "Induction of Differentiation of Leukemia Cells in Vitro by N-Substituted Amides, Lactams, and 2-Pyridones," Journal of Medicinal Chemistry, 24(9):1092-1094 (1981).
Malley, et al., "Chronic Toxicity and Oncogenicity of N-methylpyrrolidone (NMP) in Rats and Mice by Dietary Administration," Drug and Chemical Toxicology, 24(4):315-338 (2001).
Supplementary European Search Report, EP 11797384, mailed on Oct. 29, 2013. 5 pages.

\* cited by examiner

*Primary Examiner* — Uma Ramachandran
(74) *Attorney, Agent, or Firm* — Cooley LLP

(57) ABSTRACT

Methods of treatment or prevention of a cancerous or pre-cancerous condition, of slowing or preventing growth of a cancerous condition, of stimulating a cell-mediated immune response, stimulating a Th1 helper T cell response against a pathogen in a mammal and of treating or preventing inflammatory diseases or disorders that involve administration of N-methyl pyrrolidone (NMP) or a physiologically acceptable salt, solvate, tautomer or prodrug thereof are provided. Also provided are formulations of an active agent.

5 Claims, 9 Drawing Sheets

(a) Overall survival (Vk*MYC mice)

(b) Immunoglobulin light chain secretion (c)

(d)

(e)

(f)

STIMULATING IMMUNE RESPONSE

CROSS-REFERENCES TO RELATED APPLICATIONS

This application is a U.S. national phase application of International PCT Patent Application No. PCT/AU2011/000752, which was filed on Jun. 21, 2011, which claims priority to Australian Patent Application No. 2010902717, filed Jun. 21, 2010. These applications are incorporated herein by reference in their entireties.

FIELD OF THE INVENTION

The invention relates to methods of treatment or prevention of a cancerous or pre-cancerous condition, of slowing or preventing progression of a cancerous condition and to related uses. The invention also relates to methods of stimulating a cell-mediated immune response and stimulating a Th1 helper T cell response against a pathogen in a mammal and well as to methods of treating or preventing inflammatory disorders or diseases.

BACKGROUND OF THE INVENTION

Cancer is characterized primarily by an increase in the number of abnormal immortal cells derived from a given normal tissue, invasion of adjacent tissues by these abnormal cells, loss of normal cell function and lymphatic or blood-borne spread of malignant cells to regional lymph nodes and to distant sites (metastasis). Clinical data and molecular biological studies indicate that cancer is a multistep process that begins with minor pre-neoplastic changes, which may under certain conditions progress to neoplasia. Neoplastic lesions may evolve clonally and develop an increasing capacity for invasion, growth, metastasis, and heterogeneity, especially under conditions in which the neoplastic cells escape the host's immune surveillance.

There is an enormous variety of cancers that are described in detail in the medical literature. Examples include cancer of the lung, colon, rectum, prostate, breast, brain, skin, blood cells and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer, to prevent the development of pre-cancerous conditions into cancer and to slow cancer progression.

Current cancer therapies may involve surgery, chemotherapy, hormonal therapy and/or radiation treatment to eradicate neoplastic cells in a patient. More recently, cancer therapies may also involve biological therapy or immunotherapy. All of these approaches pose significant drawbacks for the patient. Surgery, for example, may be contraindicated due to the health of a patient or the location of the tumour. In any case, surgery may not completely remove neoplastic tissue. Radiation therapy is only effective when the neoplastic tissue exhibits a higher sensitivity to radiation than normal tissue. Radiation therapy often elicits serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Despite availability of a variety of chemotherapeutic agents, chemotherapy has serious drawbacks. Almost all chemotherapeutic agents are toxic, and chemotherapy causes significant, and often dangerous, side effects including severe nausea, bone marrow depression, and immunosuppression. Additionally, even with administration of combinations of chemotherapeutic agents, many tumor cells are resistant or develop resistance to chemotherapy. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. As a result of drug resistance, many cancers prove refractory to standard chemotherapeutic treatment protocols.

There is a significant and growing need for safe and effective agents and methods for treating, preventing and managing cancer. There is also an increasing need to develop agents and methods that can activate or stimulate an immune response within subjects not only in the context of cancer therapy, but also in response to challenge by other pathogens such as bacteria, viruses, protists, prions, fungi and helminths. This is especially the case in treatment of bacterial infections, in view of the increasing phenomenon of bacterial resistance to antibiotic agents.

SUMMARY OF THE INVENTION

According to one embodiment of the present invention there is provided a method of treatment or prevention of a cancerous or pre-cancerous condition in a mammalian subject which comprises administering to the subject an effective amount of N-methylpyrrolidone (NMP) or a physiologically acceptable salt, solvate, tautomer or prodrug thereof.

In another embodiment of the invention there is provided a method of slowing or preventing progression of a cancerous or pre-cancerous condition in a mammalian subject which comprises administering to the subject an effective amount of N-methylpyrrolidone (NMP) or a physiologically acceptable salt, solvate, tautomer or prodrug thereof.

In a further embodiment of the invention there is provided use of N-methylpyrrolidone (NMP) or a physiologically acceptable salt, solvate, tautomer or prodrug thereof in treatment or prevention of a cancerous or pre-cancerous condition in a mammalian subject.

In a further embodiment of the invention there is provided use of N-methylpyrrolidone (NMP) or a physiologically acceptable salt, solvate, tautomer or prodrug thereof in preparation of a medicament for treatment or prevention of a cancerous or pre-cancerous condition in a mammalian subject.

In a further embodiment of the invention there is provided use of N-methylpyrrolidone (NMP) or a physiologically acceptable salt, solvate, tautomer or prodrug thereof in slowing or preventing progression of a cancerous or pre-cancerous condition in a mammalian subject.

In a further embodiment of the invention there is provided use of N-methylpyrrolidone (NMP) or a physiologically acceptable salt, solvate, tautomer or prodrug thereof in preparation of a medicament for slowing or preventing progression of a cancerous or pre-cancerous condition in a mammalian subject.

In a further embodiment of the invention there is provided a method of stimulating a cell-mediated immune response against a pathogen in a mammalian subject which comprises administering to the subject an effective amount of N-methylpyrrolidone (NMP) or a physiologically acceptable salt, solvate, tautomer or prodrug thereof.

In a further embodiment of the invention there is provided use of N-methylpyrrolidone (NMP) or a physiologically acceptable salt, solvate, tautomer or prodrug thereof in stimulating a cell-mediated immune response against a pathogen in a mammalian subject.

In a further embodiment of the invention there is provided use of N-methylpyrrolidone (NMP) or a physiologically acceptable salt, solvate, tautomer or prodrug thereof in preparation of a medicament for stimulating a cell-mediated immune response against a pathogen in a mammalian subject.

In a further embodiment of the invention there is provided a method of stimulating a Th1 helper T cell response against a pathogen in a mammalian subject which comprises administering to the subject an effective amount of N-methylpyrrolidone (NMP) or a physiologically acceptable salt, solvate, tautomer or prodrug thereof.

In a further embodiment of the invention there is provided a use of N-methylpyrrolidone (NMP) or a physiologically acceptable salt, solvate, tautomer or prodrug thereof in stimulating a Th1 helper T cell response against a pathogen in a mammalian subject.

In a further embodiment of the invention there is provided use of N-methylpyrrolidone (NMP) or a physiologically acceptable salt, solvate, tautomer or prodrug thereof in preparation of a medicament for stimulating a Th1 helper T cell response against a pathogen in a mammalian subject.

In a further embodiment of the invention there is provided a method of stimulating a natural killer (NK) cell response against a pathogen in a mammalian subject which comprises administering to the subject an effective amount of N-methylpyrrolidone (NMP) or a physiologically acceptable salt, solvate, tautomer or prodrug thereof.

In a further embodiment of the invention there is provided a use of N-methylpyrrolidone (NMP) or a physiologically acceptable salt, solvate, tautomer or prodrug thereof in stimulating a natural killer (NK) cell response against a pathogen in a mammalian subject.

In a further embodiment of the invention there is provided use of N-methylpyrrolidone (NMP) or a physiologically acceptable salt, solvate, tautomer or prodrug thereof in preparation of a medicament for stimulating natural killer (NK) cell response against a pathogen in a mammalian subject.

In a further embodiment of the invention there is provided a pharmaceutical or veterinary composition comprising N-methylpyrrolidone (NMP) or a physiologically acceptable salt, solvate, tautomer or prodrug thereof as active ingredient in combination with one or more physiologically acceptable carriers and/or diluents.

In a further embodiment of the invention there is provided an agent for treatment or prevention of a cancerous or pre-cancerous condition, for stimulating a cell-mediated immune response against a pathogen, for stimulating a Th1 helper T cell response against a pathogen or for stimulating a natural killer (NK) cell response against a pathogen in a mammalian subject which comprises N-methylpyrrolidone (NMP) or a physiologically acceptable salt, solvate, tautomer or prodrug thereof as active ingredient.

In another aspect of the invention there is provided a method of treating or preventing an inflammatory disease or disorder in a mammalian subject which comprises administering to the subject an effective amount of N-methylpyrrolidone (NMP) or a physiologically acceptable salt, solvate, tautomer or prodrug thereof.

In a further aspect of the invention there is provided use of N-methylpyrrolidone (NMP) or a physiologically acceptable salt, solvate, tautomer or prodrug thereof treating or preventing an inflammatory disease or disorder in a mammalian subject.

In a still further aspect of the invention there is provided use of N-methylpyrrolidone (NMP) or a physiologically acceptable salt, solvate, tautomer or prodrug thereof in preparation of a medicament for treating or preventing an inflammatory disease or disorder in a mammalian subject.

Preferably the methods, uses, agents or compositions of the invention involve or comprise NMP.

BRIEF DESCRIPTION OF THE FIGURES

In further describing the invention reference will be made to the accompanying drawings in which.

The supernatants were harvested and analysed for IL1beta (a), GM-CSF (b) and IL6 (c) and TNF-alpha production (pg/ml).

Figure 8:
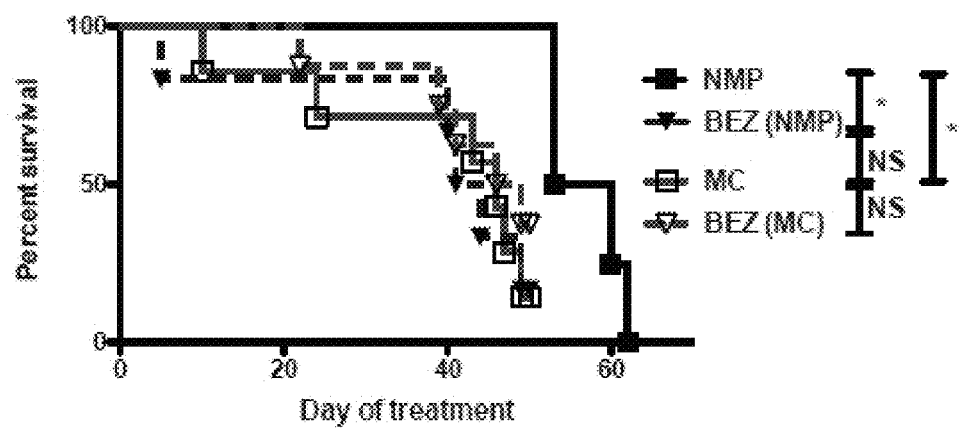
Figure 8:
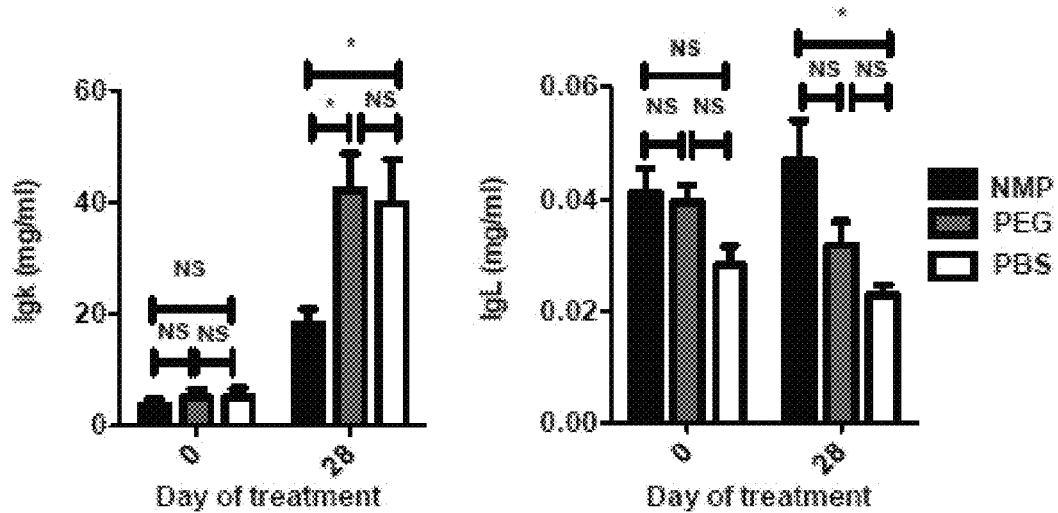
Figure 8:
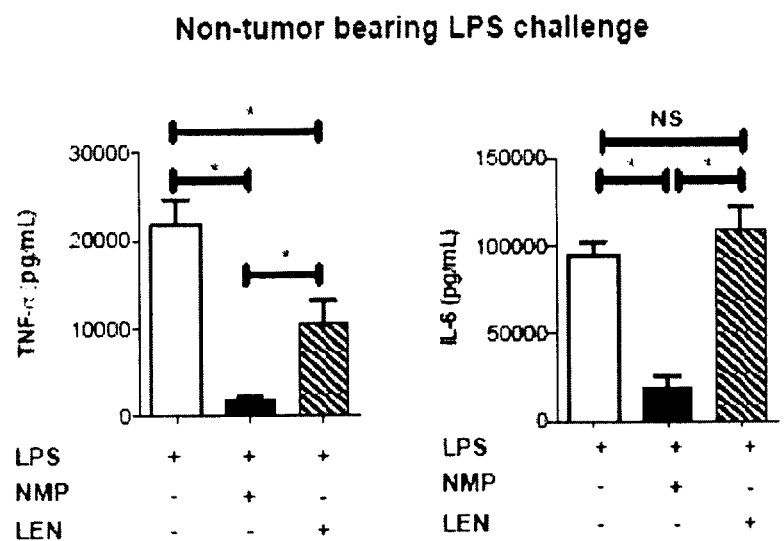
Figure 8:
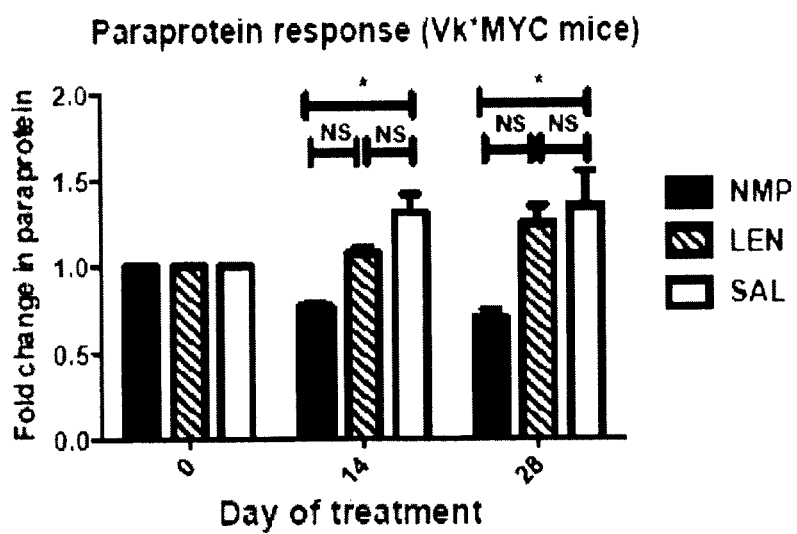
Figure 8:
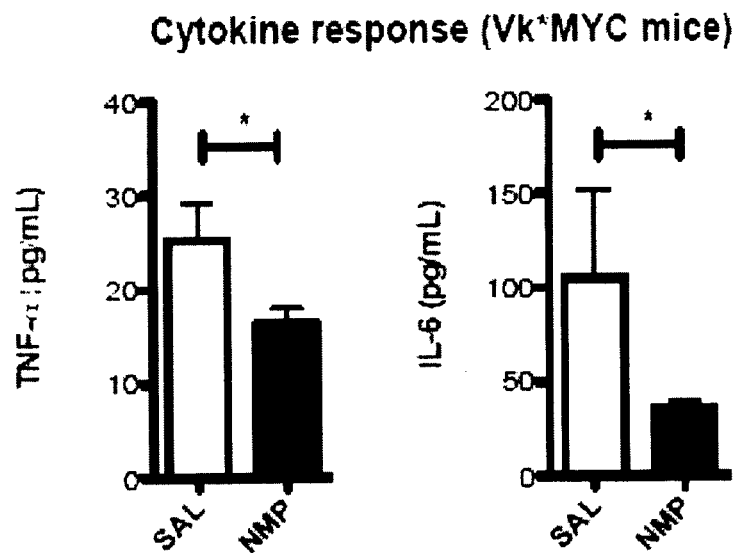
Figure 8:
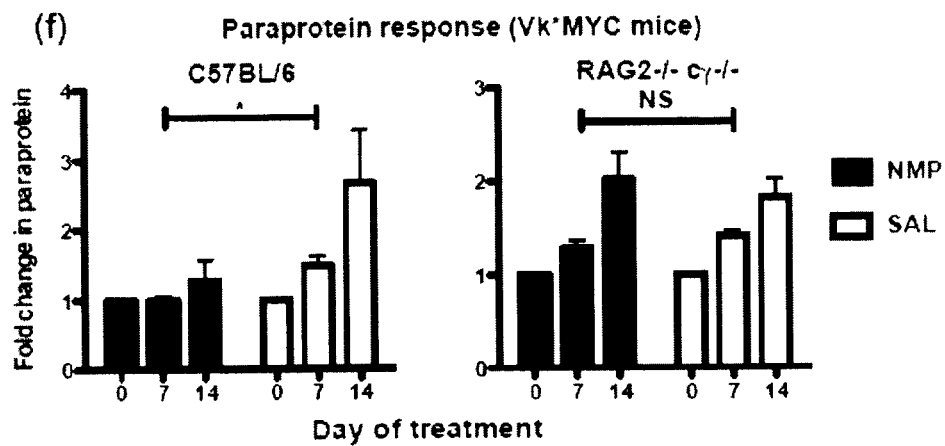

FIG. 8. NMP has in vivo anti-MM activity. (a) Overall survival in mice bearing transplanted Vk*MYC MM was prolonged in NMP/PEG (NMP) treated mice (n=4, median survival 56.5d) compared to methylcellulose (MC) controls (n=7, median survival 46d). Concurrent administration of the PI3K/mTOR inhibitor BEZ235 (BEZ, 25 mg/kg/d; n=6, median survival 42.5d) antagonized the therapeutic effect of NMP. BEZ235 treatment in MC vehicle had minimal effect of disease progression (n=8, median survival 47.5d). (b) Matched cohorts of mice bearing Vk*MYC MM were treated with NMP/PEG (NMP, n=15), PEG alone (PEG, n=10) or PBS (n=7). Suppression of clonally secreted Ig Kappa (K) was dependent on NMP exposure. Residual polyclonal Ig Lambda (L) was less suppressed in the NMP treated mice. (c) Serum cytokine levels from non-tumor bearing mice 4 hours after LPS challenge alone (n=14) or LPS and pre-treatment with either NMP/PEG (n=9) or Lenalidomide (LEN, 100 mg/kg; n=10). (d) Lenalidomide (100 mg/kg, n=4) has poor efficacy compared with NMP (n=4) against Vk*MYC MM in vivo. Control mice were treated with 0.9% saline (SAL, n=6). (e) Serum cytokine levels from tumor bearing mice following one week of treatment with SAL (n=8) or NMP (n=8). (f) Comparative NMP responses in C57BL/6 (NMP n=8; SAL n=7) and Rag2$^{-/-}$cy$^{-/-}$ knockout (NMP n=6; SAL n=9) mice transplanted with the same Vk*MYC clone. No response to NMP was seen in the immunodeficient mice. PBS, phosphate buffered saline; Ig, immunoglobulin. Data are presented as mean+/−SEM. NS, not statistically significant, p≥0.05; *p<0.05.

Figure 9:
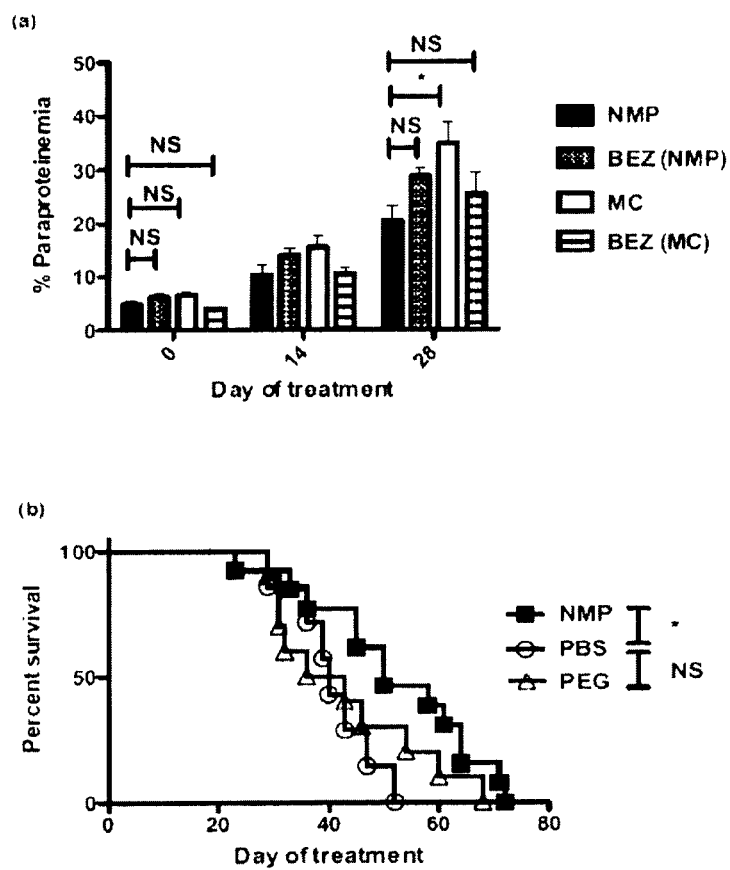

FIG. 9. (a) NMP/PEG-treated mice (n=15, median survival 50d) showed delayed progression of paraproteinemia and improved survival (b) compared to PBS-treated mice (n=7, median survival 40d). By contrast, PEG-alone treated mice (n=10, median survival 39.5d) do not differ from the PBS cohort.

Figure 10:
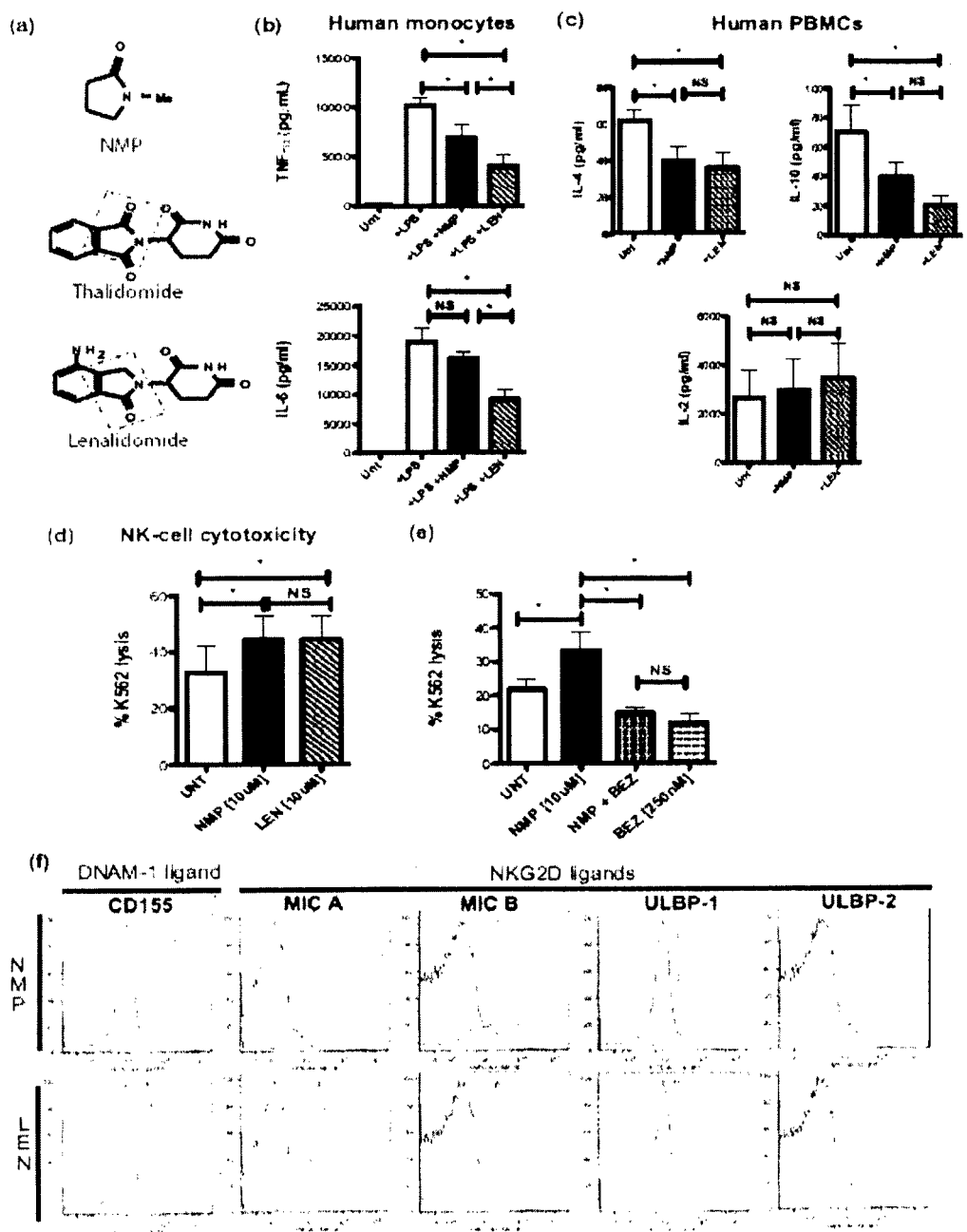

FIG. 10. NMP possesses immunomodulatory activity in vitro (a) The chemical structures of NMP, thalidomide and lenalidomide. (b) The anti-inflammatory potential of NMP was assessed using LPS-treated CD14+ monocytes that were isolated from healthy donor PBMC. Monocytes were treated with 10 uM NMP or lenalidomide (LEN) and 1 ug/mL LPS for 18 hr or left untreated (Unt), then supernatants were analyzed via cytokine bead array for TNFα and IL-6. (c) The polarizing effect of NMP on cytokine production from PBMC was assessed from supernatants collected after 3d drug treatment. Levels of IL-2, IL-4 and IL-10 were analyzed by cytokine bead array. (d) NK-cell cytotoxicity was assessed by culturing healthy donor PBMC in the presence of 10 uM NMP, 10 uM lenalidomide, or as media alone (Unt). Cells harvested after 3d were washed and used as effectors in chromium release assays against the NK-only sensitive cell line, K562 at an effector ratio of 50:1. (e) NMP induced cytotoxicity was downregulated by co-treatment with the dual PI3K/mTOR inhibitor BEZ235 (250 nM) (f) The ability of NMP to sensitize myeloma cells to NK cell lysis was assessed by treating U266 cells with 10 uM NMP or lenalidomide for 48 hrs, followed by flow cytometric analysis of the NKG2D ligands (MIC-A, MIC-B, ULBP-1, ULBP-2) and the DNAM-1 ligand CD155 (black line refers to unstained cells, blue line to basal level expression, red line to post drug treatment). Data are presented as mean+/−SEM. NS, not statistically significant. (p≥0.05), *p<0.05

DETAILED DESCRIPTION OF THE INVENTION

Throughout this specification, unless the context requires otherwise, the word "comprise", or variations such as "comprises" or "comprising", will be understood to imply the inclusion of a stated integer or group of integers but not the exclusion of any other integer or group of integers.

The reference to any prior art in this specification is not, and should not be taken as, an acknowledgment or any form of suggestion that that prior art forms part of the common general knowledge in Australia.

The compound N-methylpyrrolidone (also variously known as 1-methyl-2-pyrrolidone, M-pyrol®, 1-methyl-2-pyrrolidinone, 1-methylpyrrolidin-2-one, methylpyrrolidinone, methylpyrrolidone and NMP), which will be referred to throughout as 'NMP', is a commercially available and widely used industrial solvent, which has been used as an excipient in topical human pharmaceutical and cosmetic agents, as a solubilising agent in parenteral and topical veterinary medicines and in preparation of cement for joint prostheses. It therefore has a well understood pharmacokinetic profile and is rapidly and extensively metabolised and excreted. NMP is generally considered to be substantially biologically inert, and it is for these reasons that it has been considered appropriate for use as a drug delivery vehicle, particularly for compounds that are poorly soluble in aqueous solution and intended for oral administration. A polymeric form of NMP, polyvinyl-pyrrolidone (PVP) has also been extensively used as an excipient in pharmaceutical formulations.

The chemical structure of NMP is provided below:

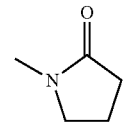

Chemical Structure of 1-methyl-2-pyrrolidone
(NMP)

A large body of literature exists in relation to the delivery to mice of pre-clinical compounds (such as kinase inhibitors) diluted in NMP or in a mixture of NMP and polyethyleneglycol (PEG)-300 at a 1:10 volume to volume ratio. There is no report in this literature of anti-neoplastic or immunomodulatory effects of NMP. Surprisingly, however, the present inventors have demonstrated in a mouse myeloma model involving mice with a functional immune system, that NMP exhibits anti-myeloma activity. Further studies subsequently conducted have demonstrated that NMP exhibits immunomodulatory activity and the present inventors have shown that this activity is modulated by enhancement of natural killer (NK) cell cytotoxic effector function and stimulation of Th-1 helper T cells. It has also been demonstrated by the present inventors that NMP exhibits inhibition of inflammatory cytokines such as IL-1b, GM-CSF, IL-6 and TNF-α, albeit at a somewhat lower level at least in vitro than the known IMID Lenalidomide (Len). Significantly, NMP has been shown in in vivo mice models to demonstrate improved inhibitory activity against inflammatory cytokines, and especially against IL-6, in comparison to Len. This indicates that NMP will be effective in treatment of inflammatory conditions. NMP also has advantageous activity in comparison to Len in a model of myeloina, as it exhibits a single-agent anti-myeloma effect. This is consistent with the observation that NMP inhibits IL-6, which is an important myeloma cell growth factor.

In addition to administration in the therapies according to the present invention of NMP itself, the invention also encompasses administration of physiologically acceptable salts, solvates, tautomers or prodrugs of NMP, which collectively are referred to herein as 'compounds of the invention'.

The salts of NMP are physiologically suitable in the sense that they are suitable for administration to mammals, and particularly to humans, such as in pharmaceutical or veterinary formulations. Examples of physiologically acceptable salts include salts of physiologically acceptable cations such as sodium, potassium, lithium, calcium, magnesium, ammonium and alkylammonium; acid addition salts of physiologically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicyclic, sulphanilic, aspartic, glutamic, edetic, stearic, palmitic, oleic, lauric, pantothenic, tannic, ascorbic and valeric acids.

The term "pro-drug" is used herein in its broadest sense to include those compounds which are converted in vivo to NMP or to its physiologically acceptable salts, solvates or tautomers.

The term "tautomer" is used herein in its broadest sense to include forms of NMP which are capable of existing in a state of equilibrium between two different isomers. Tautomers may differ in the bond connecting two atoms or groups and the position of these atoms or groups in the compound. This term in particular encompasses keto-enol tautomers.

The compounds administered according to the invention may be electrically neutral or may be in the form of polycations with associated anions for electrical neutrality. Suitable associated anions include sulphate, tartrate, citrate, chloride, nitrate, nitrite, phosphate, perchlorate, halosulfonate or trihalomethylsulfonate.

Methods of this invention encompass methods of treating and preventing cancerous or pre-cancerous conditions and slowing or preventing progression of cancerous or pre-cancerous conditions. As used herein, unless otherwise specified, the term "treating" refers to the administration of a compound of the invention after the onset of symptoms of the particular disease or disorder. As used herein, unless otherwise specified, the term "preventing" refers to the administration prior to the onset of symptoms, particularly to patients at risk of cancer. Patients with familial history of cancer or pre-cancerous conditions or patients diagnosed with a pre-disposure to a cancerous condition are those for whom preventative therapies are most appropriate.

Cancer progression is associated with increasing number and/or size of solid tumours, increasing proportion of cancer cells relative to healthy haematological cells and metastasis of primary tumour to secondary sites. By reference to 'slowing or preventing progression of a cancerous or pre-cancerous condition' it is intended to convey that the rate of growth in size or number of solid tumours or of the proportion of cancer cells compared to healthy blood cells is slowed or stopped relative to the untreated situation, or that the rate of metastatic events is slowed or prevented. In many cases the best determination of slowing of cancer progression can be made by analysing cancer or pre-cancerous disease markers specific for the particular condition.

As used herein, the term 'cancer' includes, but is not limited to, solid tumors and blood born cancers. The term refers to neoplastic disease, that is abnormal proliferation of cells, for example of skin tissues, organs, blood, and vessels, including, but not limited to, bladder, bone or blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Neoplastic disease or abnormal cellular proliferation includes that related to both cancerous and pre-cancerous conditions, where pre-cancerous neoplastic disease has the potential to develop into cancerous or malignant disease, characterised by anaplasia and metastasis. Cancerous conditions are characterised by uncontrolled cellular proliferation, loss of cell specialisation, invasiveness into nearby tissues, cellular immortality and, ultimately, metastasis.

Specific cancers that can be treated according to methods of the invention include, but are not limited to, amyloidosis, neuroblastoma, meningioma, hemangiopericytoma, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, chronic lymphocytic leukaemia, chronic myeloid leukaemia, acute lymphoblastic leukaemia, acute myeloid leukemia and related precursor neoplasms, AML with myelodysplasia related changes, myelodysplastic syndromes, myelodysplastic syndrome with isolated del(5q) Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, multiple myeloma, smoldering myeloma, indolent myeloma, non-secretory myeloma, plasma cell leukaemia, solitary plasmacytoma, osteosclerotic myeloma/POEMS syndrome, monoclonal gammopathy of undetermined significance, multicentric Castlemann's disease, lymphoplasmacytic lymphoma, monoclonal light and heavy chain deposition diseases, heavy chain diseases, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation. The methods according to the present invention are particularly suited to treatment and prevention and to preventing or slowing progression of multiple myeloma, and related plasma cell neoplasms and including clonal immunoglobulin deposition diseases.

This invention encompasses methods of treating patients who have been previously treated for cancer or pre-cancerous conditions, but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogenous clinical manifestations and varying clinical outcomes, the treatment given to a patient may vary, depending on his/her prognosis and other factors such as the age, heights, weight, sex, pregnancy status and general health and fitness. The skilled clinician will be able to readily determine without undue experimentation specific secondary agents, types of surgery, and types of non-drug based standard therapy that can be effectively used to treat an individual patient with cancer and other diseases or disorders.

In one embodiment of the invention compounds of the invention can be administered orally and in single or divided daily doses in an amount of from about 0.10 to about 150 mg/day. For example, compounds of the invention may be administered in an amount of from about 0.1 to about 1 mg per day, from about 0.1 to about 5 mg every other day, from about 5 to 25 mg per day, or alternatively from about 10 to about 50 mg every other day. In a specific embodiment, compounds of the invention may be administered for example, in an amount of about 1, 2, or 5 mg per day to patients with multiple myeloma.

Specific methods of the invention comprise administering a compound of the invention in combination with one or more other active agents, and/or in combination with other therapies, such as radiation therapy, blood transfusions, or surgery. Administration of the compounds of the invention and the other active agents to a patient can occur simultaneously, sequentially or separately by the same or different routes of administration. The suitability of a particular route of administration employed for a particular active agent will depend on the active agent itself (e.g., whether it can be administered orally without decomposing prior to entering the blood stream) and the condition being treated.

Agents that may, for example, be administered in combination with compounds of the invention include chemotherapeutic or anti-cancer agents (for example including bleomycin, doxorubicin, adriamycin, 5FU, neocarcinostatin, platinum drugs such as cis-platin, taxol, methotrexate, alkylating agents and other agents that produce DNA adducts) or other agents such as antibiotics, antivirals, anti-inflammatory agents including steroids and NSAIDS, hormones, growth factors, cytokines, antibodies and kinase inhibitors. Other specific examples of anti-cancer agents include: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; bortezomib; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginin deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; dioxamycin; diphenyl spiromustine; docetaxel; docosanol; dolasetron; doxifluridine; doxorubicin; droloxifene; dronabinol; duocarmycin; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib, imiquimod; immunostimulant peptides; insulin-like growth factor-1 receptor inhibitor; interferon agonists; interferons; interleukins; iobenguane; iododoxorubicin; ipomeanol, iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human, chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhithxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; spienopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific active agents that may be administered in conjunction with compounds of the invention, or which may be combined within compositions with compounds of the invention include, but are not limited to, bleomycin, bortezomib, oblimersen, remicade, docetaxel, celecoxib, melphalan, dexamethasone, steroids, gemcitabine, temozolomide, etoposide, cyclophosphamide, temodar, carboplatin, procarbazine, gliadel, tamoxifen, topotecan, methotrexate, Arisas, taxol, taxotere, tamoxifen, Gleevec, Herceptin, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin, ganciclovir, adriamycin, estramustine sodium phosphate, sulindac, and etoposide.

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the other active agent will depend on the specific agent used, the type of disease being treated or managed, the severity and stage of disease, and the amount of compounds of the invention and any optional additional active agents concurrently administered to the patient.

The present invention relates to treatments for mammalian animals, and particularly humans. Examples of non-human mammalian animals that may be treated according to the invention include experimental animals (eg. mouse, rat, guinea pig, rabbit), companion animals (eg. cat, dog), agricultural animals (eg. horse, cattle, sheep, donkey, goat, pig), and captive wild animal such as apes, monkeys, lions, tigers, elephants and the like.

The compounds of the invention may be conjugated to agents, for example, via an interactive or linking group, which will specifically deliver them to a desired tumour site.

Suitable agents may include antibodies or proteins, such as, growth factors, for example, haemopoietic growth factor which will enable preferential delivery to haemopoietic cells. The term "interactive group" is used herein in its broadest sense and refers to a group capable of forming a bond with a specific group on a target molecule or agent such as a protein or a derivative thereof. Examples of interactive groups that may be chemically bound to compounds of the invention include $N(CH_2)_n COOH$, $N(CH_2)_n CO(CH_2)_m R$, $N(CH_2)_n$—SH, $N(CH_2)_n$—$NH_2$, $CH(CH_2)_n COOH$, $CH(CH_2)_n CO(CH_2)_m R$, $CH(CH_2)_n$—SH and $CH(CH_2)_n$—$NH_2$ wherein n is 1 to 10, m is 0 to 10 and R is optionally substituted alkyl.

The compounds of the invention may be administered for therapy by any suitable route, including oral, rectal, nasal, topical (including buccal and sublingual), vaginal, intravesical and parenteral (including subcutaneous, intramuscular, intravenous, intasternal and intradermal). Preferably, administration will be by the oral route, however it will be appreciated that the preferred route will vary with the condition and age of the subject, the tissue/tumour being treated, its location within the subject and the judgement of the physician or veterinarian. The compounds of the invention may be administered directly into tissues surrounding or proximal to tumours to be treated.

The present invention also extends to a compositions which comprises NMP or salts, solvates, tautomers or prodrugs thereof, which act as active ingredient, in association with one or more physiologically (that is pharmaceutically or veterinarily) acceptable carriers and/or diluents. By the statement that the compounds of the invention are present as active ingredient in the composition or treatment method it is intended to convey that the agent is included because of its intended pharmacodynamic effect. That is, it is not merely present for the purpose of acting as a carrier, excipient or diluent agent, but is included for the purpose of exhibiting a pharmacological effect on a target within the mammalian subject, for example to treat or prevent a cancerous or pre-cancerous condition or to stimulate a cellular immune response against another pathogen.

Another aspect of the invention relates to stimulating a cell-mediated immune response against a pathogen in a mammalian subject. The pathogen in this context may be a cancer cell or an infective agent such as a bacterium, virus, fungus, protest, prion or helminth. Specific examples of viral infectious diseases include AIDS, chickenpox, common cold, cytomegalovirus infection, dengue fever, ebola, hand, foot and mouth disease, hepatitis, herpes simplex, herpes zoster, HPV, influenza, measles, infectious mononucleosis, mumps, poliomyelitis, rabies, rubella, SARS, smallpox, viral encephalitis, viral gastroenteritis, viral meningitis, viral pneumonia and yellow fever. Specific examples of bacterial infectious diseases include anthrax, bacterial meningitis, cholera, gonorrhea, legionellosis, leprosy, listeriosis, lyme disease, pneumococcal oneymonia, salmonellosis, syphilis, tetanus, tuberculosis, typhoid fever and urinary tract infectious. Specific examples of fungal infectious diseases include aspergillosis, candidiasis, coccidioidomycosis, histopplasmosis and tinea pedis. Specific examples of parasitic and prion infectious diseases include amebiasis, ascariasis, giardiasis, Leishmaniasis, malaria, scabies, toxoplasmosis, alpers syndrome, Creutzfeldt-Jakob disease, fatal familial insomnia and transmissible spongiform encephalopathy.

By the phrase 'stimulating a cell-mediated immune response' it is intended to convey that the approach results in an increase activation of macrophages, natural killer (NK) cells, antigen-specific cytotoxic T-lymphocytes and in increased release of various cytokines, but not in a significant increase in humoral immune response, which is associated with antibodies or complement activity. The compounds of the invention may therefore be administered in the form of an adjuvant in immunotherapy.

In a clinical context stimulation of a cell-mediated immune response, relative to the response without the treatment of the invention, can readily be established by assays to test for cytotoxic potential (using chromium release assays) of NK cells against K562 targets, or polyclonal cytotoxic T-lymphocytes against tumour cell lines, or clonal (ie. antigen specific) cytotoxic T-lymphocytes against targets expressing the antigen target, or loader cells (eg. T2 cells) that are loaded with the antigen target of interest. Proliferation using thymidine or CFSE can also be measured. Other assays include collection of supernatants after cellular treatment with agent of interest, then assaying for cytokine production via the Luminex instrument. Phenotypic assays to look for changes in activation and/or maturation of dendritic cells, NK cells and cytotoxic T-lymphocytes can also be measured.

Assays to measure cell-mediated immunity would include antigen-specific T cell responses. These assays may be used to detect a T cell response to a pathogen- or tumour-derived antigen, or an alloantigen. To examine the pathogen or tumour antigen T cell responses, human PBMCs are cultured with an antigen presenting cell [eg. an autologous monocyte-derived dendritic cell (MoDC)] pulsed with either pathogen/tumour-derived peptides or protein. The T cell (CD4 or CD8) response can then be detected by cytokine production, either intracellular cytokine response (TNF-α, IL-2, IFN-γ) by flow cytometry or cytokine bead array on culture supernatant. Alternative methodology to assess an antigen-specific T cell response includes the ELISPOT assay. In addition, a CFSE proliferation assay can be performed to detect CD4 or CD8 T cell proliferation in response to antigen presentation. Further, a cytotoxic T cell assay can be performed using the peptide/protein pulsed MoDCs as targets; this would be performed as a chromium release assay. To measure allogeneic T cell responses, γ-irradiated allogeneic MoDCs or PBMCs are cultured with responder CFSE-labelled PBMCs; cells are co-cultured for 5 days in the absence of exogenous cytokines. Proliferation of CD4 or CD8 T cells is detected by dilution of CFSE staining compared to undivided cells.

Methods of the invention can also be adopted for stimulating a Th1 helper T cell response against a pathogen in a mammalian subject. By the phrase 'stimulating a Th1 helper T cell response' it is intended to convey that the approach results in an increase activation of cells of the Th1 subclass of helper T cells, relative to the level of stimulation of cells of the Th2 subclass. In a clinical context stimulation of a Th1 helper T cell response, relative to the response without the treatment of the invention, can readily be established by assaying for Th1 specific cytokine production including IL-2, IL-12 and IFN-γ. Specific recognition of pathogen by cytotoxic T-lymphocytes can easily be assessed in chromium release assays using clonal cytototoxic T-lymphocytes specific for the 'flu' FMP epitope, and using T2 target cells loaded with the FMP peptide, or using EBV transformed cell lines such as LCLs as targets. For example, such assays may involve co-culturing the patient T cells with peptide/protein-pulsed autologous MoDCs. Responding antigen-specific T cells will secrete cytokines. The type, range and level of cytokine will indicate whether individual CD4 T cells have a Th1, Th2, Th0, Th17 or Treg functional status. The secretion of cytokines may be detected by intracellular cytokine staining and flow cytometry, or by cytokine bead array on the culture supernatant. Signature Th1 cytokines include IL-2 and IFN-γ.

A further aspect of the invention is the treatment or prevention of inflammatory diseases or disorders in mammalian patients, such as humans, involving the administration of NMP or salts, solvates, tautomers or pro-drugs thereof. Examples of inflammatory diseases or disorders over and above the pathogenic diseases or disorders already mentioned include autoimmune diseases such as arthritis, Crohn's disease, colitis, irritable bowel syndrome, lupus erythematous, ulcerative colitis and multiple sclerosis, respiratory diseases such as asthma, cystic fibrosis, pleurisy and pharyngitis, gastrointestinal diseases such as diverticulitis, hepatitis, Crohn's disease, colitis, irritable bowel syndrome, nephritis, ulcerative colitis, celiac disease, gastritis, splenitis and hepatitis, neurological diseases such as Alzheimer's, Parkinson's, neuropathy and multiple sclerosis and joint/connective tissue/skin or mucous membrane diseases such as arthritis, atherosclerosis, lupus erythematous, tendonitis, sinusitis, laryngitis, cystic fibrosis, bursitis, gingivitis, conjunctivitis, gout, psoriasis, eczema, vasculitis, thyroiditis, sarcoidosis, myopathy, Wegener's granulomatosis and seborrheic dermatitis.

The compositions of the present invention comprise a compound of the invention together with one or more physiologically or pharmaceutically acceptable carriers, diluents, adjuvants and/or excipients and optionally other medicaments. Each carrier, diluent, adjuvant and/or excipient must be physiologically or pharmaceutically "acceptable" in the sense of being compatible with the other ingredients of the composition and not injurious to the subject. Compositions include those suitable for oral, rectal, nasal, topical (including buccal and sublingual), vaginal, intravesical or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier, which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product. Further details of conventional pharmaceutical compositions are explained in Remington's Pharmaceutical Sciences, 18$^{th}$ Edition, Mack Publishing Co., Easton, Pa., USA, the disclosure of which is included in its entirety by way of reference.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or as granules, optionally mixed with a binder (e.g. cross-linked povidone, cross-linked sodium carboxymethyl cellulose), inert diluent, preservative, disintegrant (e.g. sodium starch glycollate), surface-active agent and/or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured basis, usually sucrose and acacia or tragacanth gum; pastilles comprising the active ingredient in an inert basis such as gelatin and glycerin, or sucrose and acacia gum; and mouthwashes or sprays comprising the active ingredient in a suitable liquid carrier.

For topical application to the skin, the active ingredient may be in the form of a cream, ointment, jelly, solution or suspension.

For topical application to the eye, the active ingredient may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine and thickening agents such as hypromellose may also be included.

Compositions for rectal administration may be presented as a suppository with a suitable non-irritating excipient which is solid at ordinary temperatures but liquid at the rectal temperature and will therefore melt in the rectum to release the active ingredient. Such excipients include cocoa butter or a salicylate.

Nasal compositions may be presented topically as nose drops or sprays or systemically in a form suitable for absorption through the nasal mucosa and/or the alveolar cells in the lungs.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The compounds of the invention may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intra-mammary injection where a suspension or solution is introduced into the udder via the teat;
(c) topical application, e.g. as a cream, ointment or spray applied to the skin; or
(d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

It should be understood that the present invention has been described above by way of example only, and that modifications and/or alterations that would be apparent to a person skilled in the art based upon the disclosures herein are also considered to fall within the spirit and scope of the invention. The invention will now be further described with reference to the following non-limiting examples.

Example 1—Effect of NMP on Survival of Myeloma Transplanted Mice

To test the hypothesis that NMP/PEG (N-methyl pyrrolidone/polyethyleneglycol) has anti-myeloma activity in vivo, a definitive experiment using the Vk*myc myeloma model was conducted. Importantly, these mice have an intact immune system, and can therefore respond appropriately to immune-modulatory compounds. Much of the published pre-clinical data where NMP/PEG has been used as a drug delivery vehicle has used immune-deficient xenograft models, and thus would be insensitive to the detection of a drug working by immune-modulation.

Materials and Methods

Sublethally (6Gy) irradiated C57BL/6 mice were injected with 1×10e5 Vk*myc splenocytes derived from myelomatous mice by intravenous injection. Recipient mice were monitored by serum protein electophoresis for development of monoclonal paraproteinaemia (M-spike). The monoclonal paraprotein is a sensitive and specific marker of myeloma burden, as this protein is only produced by myeloma cells. Paraprotein estimation is a standard clinical parameter by which myeloma is monitored in human patients. Once detected, M-spikes were quantitated by densitometry (expressed as % of total serum protein). With the onset of measurable disease, mice were randomly allocated (7 per cohort) to receive NMP/PEG (1:10 ratio v/v, 10 uL per gram body weight—i.e. 20 uL NMP per 20 g mouse) or inactive vehicle 0.5% methylcellulose, by daily oral administration for 60 days. Mice were monitored by weekly M-spike quantification and for clinically apparent disease. Mice developing distress due to disease progression (e.g. hind limb paralysis, splenic rupture) were euthanased.

Results

Figure 1:
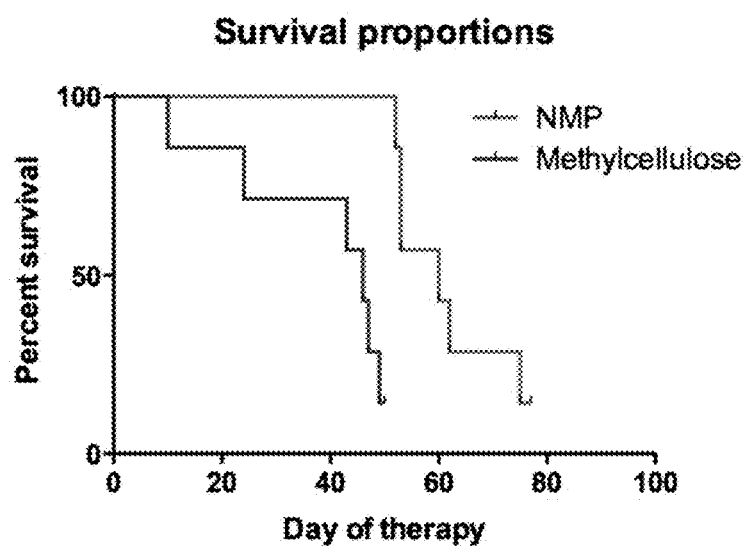
FIG. 1 shows a graph of the percent survival against the day of therapy for sub-lethally (6Gy) irradiated C57BL/6 mice injected with $1\times10^5$ Vk*myc splenocytes subsequently administered (daily for 60 days) either 1:10 v/v NMP/PEG or 0.5% methylcellulose at a dose of 10 μL per gram of body weight.
Figure 2:
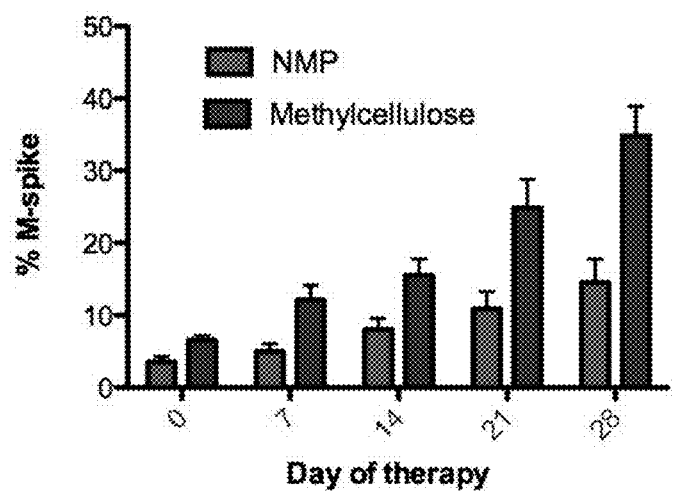
FIG. 2 shows a graph of % of monoclonal paraproteinaemia (M-spike) in total serum protein against the day of therapy for mice as treated in FIG. 1.

As is clearly shown in FIG. 1, mice in the treatment group demonstrated significantly improved survival relative to those of the control group, with the NMP treated group having a median survival of 60 days and the methylcellulose treated control group having median survival of 46 days (p=0.0013(log rank)). Further, the rate of progression of monoclonal paraproteinaemia (M-spike) was reduced in the treatment group compared to the control (FIG. 2), indicating that the NMP/PEG combination exhibits anti-myeloma activity. This activity has some similarity to the activity of the IMID (immunomodulatory) drugs of which Thalidomide and its derivatives Lenalidomide and Pomalidomide are members.

Example 2—Effect of NMP on Natural Killer Cell Function

Having confirmed the in vivo anti-myeloma activity of NMP, and noting the immunomodulatory properties of the IMID drugs such as Thalidomide, experiments were conducted to determine whether NMP exhibits immunomodulatory properties. A variety of in vitro tests of immunomodulation were therefore performed, benchmarking against Lenalidomide (Len) as a potent anti-myeloma drug with immunomodulatory properties.

Materials and Methods

Healthy donor peripheral blood mononuclear cells (PBMC) were cultured for 3 days in RPMI-1640 and 10% FCS in the presence of 10 uM NMP, 10 uM Len (positive control) or no drugs. After 3 days the cells were harvested and used as effectors in a standard 4 hr chromium release assay, using K562 as targets (natural killer (NK) only sensitive cell line) (n=3).

Results

Figure 3:
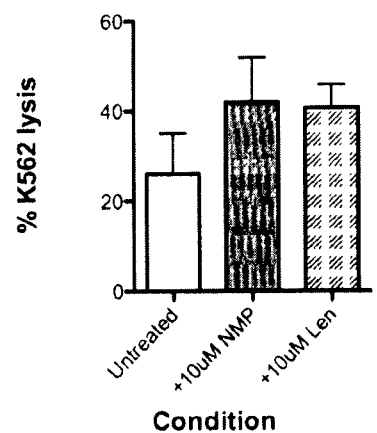
FIG. 3 shows a graph of the percent of K562 lysis for peripheral blood mononuclear cells (PBMC) cultured for 3 days with no drug (untreated), 10 μM NMP or 10 μM lenalidomide (Len) (positive control) in the culture media and then harvested and used as effectors in a chromium release assay using K562 cells (natural killer (NK) only sensitive cells).

The results provided in FIG. 3 demonstrate that relative to the untreated control NMP showed enhancement of NK cell function, and further, that this enhancement is at a comparable level to that effected by Len, at the same dose.

Example 3—Effect of NMP on Cytokine Production

These experiments were conducted in an endeavor to determine the nature of effects, if any, that NMP may have on cytokine production; in vitro.

Materials and Methods

PBMC were cultured for 3 days in RPMI-1640 and 10% FCS in the presence of 10 uM NMP, 10 uM Len or no drugs. After 3 days, supernatants were collected and a cytokine bead array performed via the Luminex instrument to analyze changes in IL-2, IL-4 and IL-10 production (n=3).

Results

Figure 4:
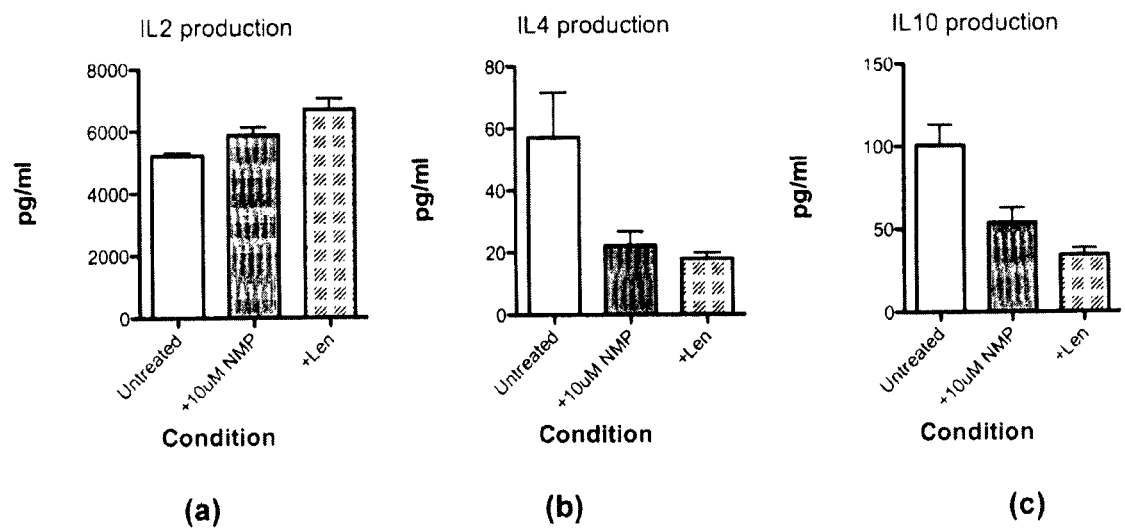
FIG. 4 shows graphs of IL2 (a), IL4 (b) and IL10 (c) production (pg/ml) for PBMC cultured for 3 days with no drug (untreated), 10 μM NMP or 10 μM lenalidomide (Len) (positive control) in the culture media, wherein the supernatant was collected and a cytokine bead array analysis was conducted.

As shown in FIGS. 4(a), (b) and (c) NMP appears to stimulate production of IL2 and inhibit IL4 and IL10 production in PBMCs, in a similar manner to Len at the same dose. This pattern of cytokine stimulation and inhibition is consistent with a Th1 helper T cell response.

Example 4—Assessment of NMP Related Cytotoxicity

This experiment was conducted to determine whether NMP is directly cytotoxic to PBMC or myeloma cells.

Materials and Methods

PBMC and a myeloma cell line (U266) were cultured in RPMI-1640 with 10% FCS in the presence of NMP (0 uM, 1 uM, 10 uM, 100 uM or 10 mM) for 48 hours. The cells were stained with viability markers (Annexin V and 7aad) and analyzed on the flow cytometer (n=2).

Results

Figure 5:
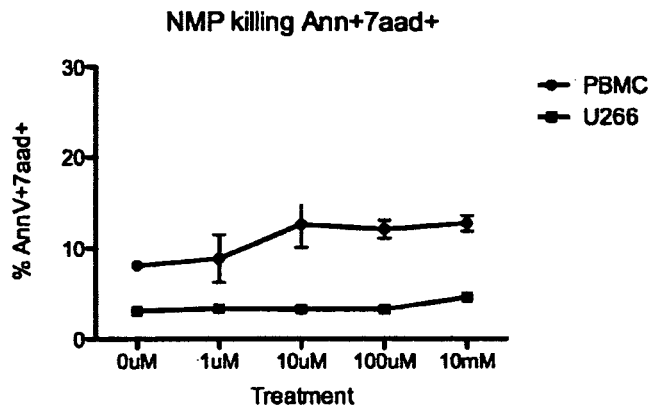
FIG. 5 shows a plot of percentage of viability markers Annexin V and 7aad (AnnV+7aad+) against the concentration (μM) of NMP for PMBC and the myeloma cell line U266 cultured in the presence of 0 μM, 1 μM, 10 μM, 100 μM and 10 μM of NMP for 48 hours.

As can be seen from FIG. 5 the level of direct cytotoxicity of NMP upon PBMC and U266 myeloma cells did not increase to any significant extent with increasing NMP dose.

Example 5—Effect of NMP on Immune Cell Subset Composition

These experiments were conducted to determine whether NMP has any effect on the proportions of immune cell subtypes.

Materials and Methods

PBMC were cultured in RPMI-1640 and 10% FCS for 3 days in the presence of either 10 uM NMP, 10 uM Len or no drugs. At day 3 the cells were harvested and stained for T cell markers (CD4 and CD8), NK markers (CD3−, CD56) and regulatory T cells (CD3, CD4, CD25, CD127low). For controls, day 0 PBMC were stained to assess changes in cellular subsets after 3 days (n=3).

Results

Figure 6:
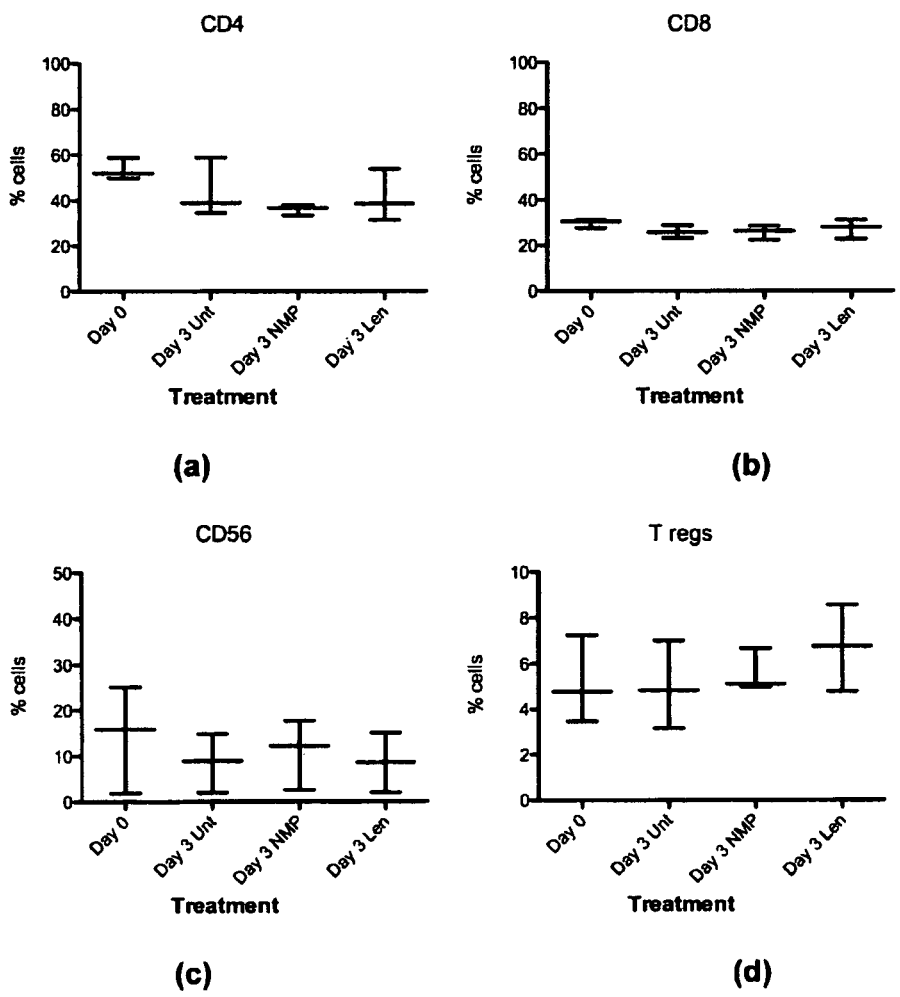
FIG. 6 shows plots of the percent of cell types for PBMC cultured for 3 days with no drug (Unt), 10 μM NMP or 10 μM lenalidomide (Len) (positive control) in the culture media and then harvested and stained for T cell markers CD4 (a) and CD8 (b), natural killer cell marker CD56 (c) and regulatory T cell markers (CD3, CD4, CD25, CD127low) (d).

As can be seen from the results shown in FIGS. 6($a$) to ($d$) there was no significant alteration in the proportions of immune cell subtypes following NMP exposure for those cell types for which markers were monitored.

Example 6—Effect of NMP on Inflammatory Cytokine Secretion

These experiments were conducted to determine whether NMP has any effect on secretion of inflammatory cytokines by CD14+ monocytes.

Materials and Methods

CD14+ monocytes were sorted via the Dynal bead kit from PBMC. The cells were then treated with LPS to induce cytokine production, and cultured overnight in the presence of 10 uM NMP, 10 uM Len or no drugs. As background controls, non LPS stimulated monocytes were used. The supernatants were harvested and IL-1beta, GM-CSF, IL-6 and TNF-alpha analyzed via the Luminex beady array assay (n=3).

Results

Figure 7:
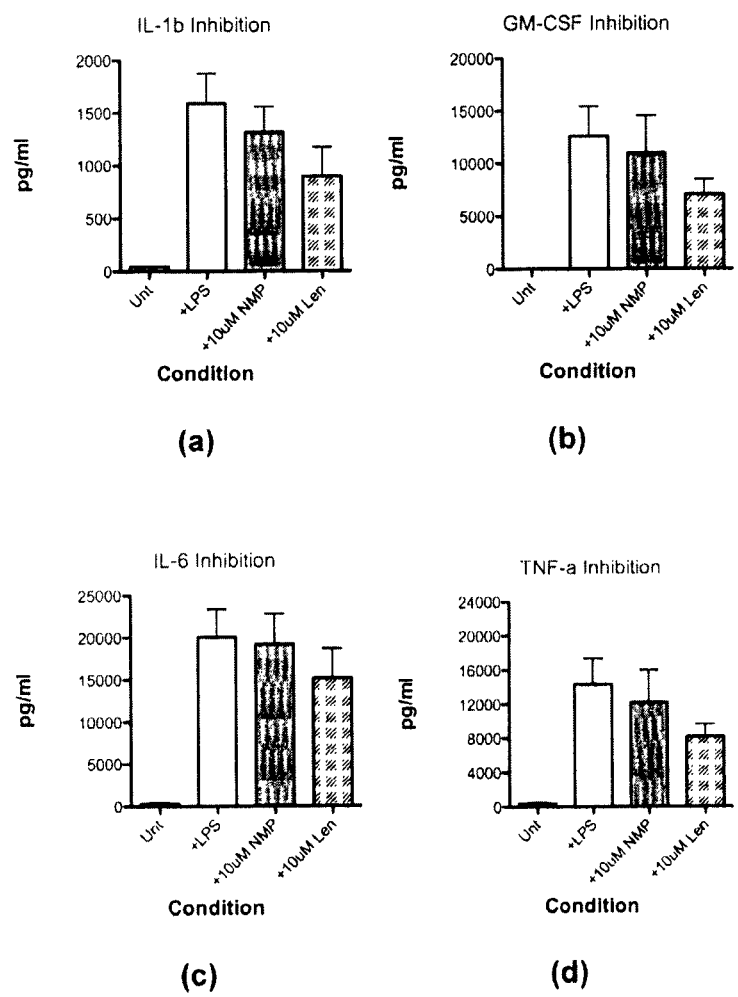
FIG. 7 shows graphs of amount of cytokine production for CD14+ monocytes sorted from PBMC and then treated with LPS to induce cytokine production and cultured overnight with no drug (+LPS), 10 μM NMP or 10 μM lenalidomide (Len) (positive control) in the culture media, or using non-LPS stimulated monocytes (Unt) (background control).

In the results provided in FIGS. 7 ($a$) to ($d$) NMP was not shown to demonstrate a statistically significant effect relative to the LPS only treated control in secretion of the four inflammatory cytokines monitored. Statistically significant inhibition of the inflammatory cytokines IL-6 and TNF-alpha is, however, shown in later work reported in FIG. 10.

Example 7—NMP Functions as an Immunomodulatory Drug

NMP is known and commercially available as a reputedly inert pharmacological delivery vehicle and industrial organic solvent. The present inventors report anti-myeloma activity of NMP, not previously recognized despite widespread use in preclinical cancer models and human patients.

Methylpyrrolidone is an organic solvent favored in industry for low volatility, thermal stability and minimal toxicity. Its applications include processing of petrochemicals, textile manufacture and paint thinner. Accordingly, attention has been given to health effects of occupational NMP exposure. NMP toxicology is well-characterized, with low acute toxicity in rodents (oral $LD_{50}$ 3600-7700 mg/kg), no genotoxicity in bacterial and mammalian tests, and no carcinogenic effects in rats after long-term exposure via inhalation or diet. The major toxic effects are reproductive, but require high exposures; the no-effect level in rats (for a decrease in pup body weight) requires 160 mg/kg/day in the diet. As NMP is considered relatively inert, it is used in pharmaceutical, preparations, cosmetics, dentistry and orthopedic cements; hence iatrogenic exposures are common.

Multiple myeloma (MM) remains an incurable plasma cell malignancy. However, MM is peculiar in its response to certain novel therapeutics including immunomodulatory drugs (IMiDs®), such as thalidomide. Thalidomide's mode of action is poorly understood, but includes stimulation of immune effector cells and suppression of inflammatory cytokines (e.g. interleukin, IL-6) that are important for myeloma cell survival. As thalidomide's molecular targets are obscure, immunomodulatory properties are used as a biomarker of IMiD® activity. For example, suppression of lipopolysaccharide (LPS) induced tumor necrosis factor (TNF)-α secretion is used to screen candidate compounds. New generation analogues (e.g. lenalidomide and pomalidomide) were built empirically on the thalidomide backbone; biologically active subunits have not been reported.

NMP has been extensively used to solubilize drugs for oral delivery, particularly kinase inhibitors that do not readily form aqueous solutions. Of note, NMP was used in the preclinical evaluation of the tyrosine kinase inhibitor, nilotinib now approved for treatment of BCR-ABL positive leukemias. More recently, NMP has become a popular vehicle for phosphatidylinositol-3-kinase (PI3K) and mammalian target of rapamycin (mTOR) inhibitors. While evaluating the PI3K/mTOR inhibitor BEZ235[1] in the transgenic Vk*MYC MM model[2], we noted improved survival and delayed progression of paraproteinemia in NMP/polyethylene glycol (PEG)-treated controls when compared to alternative vehicles (FIG. 8a and FIG. 9). This unanticipated benefit was antagonized by concurrent BEZ235, and not observed with PEG administration in the absence of NMP (FIG. 8a-b and FIG. 9). Moreover, responses were selective for clonally secreted kappa paraprotein, as residual polyclonal lambda immunoglobulins were better maintained in NMP-treated mice (FIG. 8b).

To explain this in vivo anti-MM activity, we compared NMP's chemical structure to known MM therapeutics and noted it was a core subunit of thalidomide analogues (FIG. 10a). We then tested for in vitro IMiD® activity using lenalidomide as a positive control. Similar to lenalidomide, NMP suppressed secretion of TNFα and IL-6 from LPS-stimulated monocytes (FIG. 10b). Treatment of healthy donor peripheral blood mononuclear cells (PBMC) with physiologically relevant doses of NMP or lenalidomide altered cytokine secretion away from a Th-2 profile (FIG. 10c), without altering IL-2 secretion or the proportions of CD4, CD8, NK or regulatory T cell subsets (FIG. 6a). Both NMP and lenalidomide enhanced natural killer (NK) cell cytotoxicity against K562 target cells (FIG. 10d). The augmentation of NK-cell lysis by NMP was inhibited by concurrent treatment with BEZ235 (FIG. 10e), recapitulating the antagonism observed in vivo (FIG. 8a). Having established the IMiD®-like effects of NMP on immune cells, we investigated whether NMP could alter the expression of cell surface proteins known to sensitize MM cells to NK cell lysis. NMP (1 μm-10 mM) was not cytotoxic to PBMC or the MM cell line U266 (FIG. 5). However, NMP upregulated both NKG2D and DNAM-1 ligands MIC-B, ULBP-1, ULBP-2 and CD155) on U266 cells (FIG. 10f), a property not shared by lenalidomide.

Data on the anti-MM activity of IMiDs® in murine models is limited, partly due to a lack of immunocompetent syngeneic systems. We therefore compared NMP to lenalidomide in vivo utilizing a well-established model of LPS induced inflammation and shock[3]. In non-tumor bearing mice, both NMP and lenalidomide suppressed TNFα serum levels following LPS challenge. Importantly, only NMP suppressed IL-6 production (FIG. 8c). Moreover, lenalidomide had minimal effects on the progression of transplanted Vk*MYC MM, even in indolent clones that regressed on NMP treatment (FIG. 8d). Responses in NMP-treated MM mice correlated with reductions in serum TNFα and IL-6 (FIG. 8e). Despite the previously observed interaction between BEZ235 and NMP, we did not detect any consistent effect of NMP or lenalidomide on PI3K/mTOR phosphorylation targets in vivo (not shown). To confirm the therapeutic effects of NMP were due to immune effector mechanisms, we transplanted Vk*MYC MM into $Rag2^{-/-}$ $c\gamma^{-/-}$ mice (lacking T, B or NK cells) or wild type C57BL/6 mice. NMP responses were only observed in wild type C57BL/6 and not immunocompromised mice (FIG. 8f). Together these results indicate NMP has in vivo anti-MM activity that is dependent on host immunity and associated with suppression of the plasma cell growth factor, IL-6.

These results show NMP, an agent previously thought to be biologically inert, has IMiD®-like properties and anti-MM efficacy. Importantly, our results also identify an active moiety of thalidomide. This is the first description of such activity, despite the widespread use of NMP as a drug vehicle in cancer research and toxicological analysis in the occupational exposure setting. Unexpectedly, NMP showed superior single-agent activity over lenalidomide in mice.

The poor lenalidomide efficacy may relate to inter-species variability in IMiD® metabolism between mice and humane. However, NMP may also have additional molecular targets that result in its anti-MM effects. The efficacy of lenalidomide as a single agent for newly diagnosed[5] or relapsed MM[6] is less than that achieved when combined with dexamethasone[7]. Our findings indicate that NMP can provide therapeutic activities without the need for a second agent such as corticosteroids.

The IMiD®-like properties of NMP and the low traditional toxicity of NMP make it an attractive compound to translate directly into human trials of MM and other IMiD®-responsive diseases.

Materials and Methods

Transplantation of Vk*MYC Myeloma

All mouse experiments were carried out in accordance with ethical guidelines determined by the Peter Mac Animal Experimental Ethics Committee. For in vivo assessment of NMP efficacy, treatment studies were performed on mice bearing transplanted Vk*MYC myeloma[2]. Bulk splenocytes ($1\times10^5$) derived by secondary transplantation of a primary Vk*MYC mouse exhibiting monoclonal gammopathy with end-organ MM manifestations were injected by tail vein into cohorts of sub-lethally irradiated (6Gy) C57BL/6 recipients. To exclude the potential for adoptive transfer of immune cells with grafts into $Rag2^{-/-}c\gamma^{-/-}$ mice and matched C57BL/6 recipients (FIG. 8f), freshly sorted Vk*MYC MM cells (40,000 per mouse) were used for this experiment. The onset of transplanted disease was confirmed by serum protein electrophoresis; those mice manifesting M-protein >2% of total serum protein (FIG. 8a) or >5% (remaining figures) were selected for treatment.

Dosing of Tumor Bearing Mice

All dosing was performed by oral gavage using freshly prepared drug solutions or suspensions. Mice were dosed with NMP according to standard practice for drug administration using NMP/PEG as a vehicle[1]. NMP (Sigma Aldrich, NSW, AUS) was diluted 1 in 10 v/v (FIG. 8a) or 1 in 5 v/v (remaining figures) in PEG300 (Sigma Aldrich, NSW, AUS) and administered by oral gavage to a final volume of 1 uL NMP per gram mouse weight.

BEZ235 was kindly provided by Novartis. According to Novartis' recommendations, BEZ235 was dissolved in NMP by heating briefly to 60° C. and further diluting 1 in 10 v/v in PEG300. Alternatively BEZ235 was suspended in 0.5% methylcellulose (MC) solution and mixed thoroughly prior to administration.

Lenalidomide was kindly provided by Celgene. Lenalidomide was suspended in 0.9% saline solution immediately prior to oral gavage at a dose of 100 mg/kg. Equivalent volumes of phosphate buffered saline, 0.5% MC or 0.9% SAL were administered to control mice as indicated in figure legends.

Treatment was continued daily for the first month, then weekdays only for the remainder of the indicated treatment period. Mice were culled with the development of features of overt myeloma, including permanent hind-limb paralysis and disseminated extramedullary disease.

Cytokine Bead Array

Supernatants from cultured cells or serum from VK*MYC mice were used to assess the level of individual cytokines (as specified in the methods and results section) via the Luminex cytokine bead array system. The assay was conducted according to the manufacturer instructions. Briefly, pre-mixed beads were added to 25 uL of undiluted supernatant/serum, followed by the addition of detection antibodies and streptavidin in 96 well filtered-membrane plates. The plates were run on the Luminex 200 instrument and data analysed with the xPONENT software.

In Vivo Cytokine Measurements

For LPS challenges, non-tumor bearing C57BL/6 mice were administered LPS (E. Coli 0127:B8, gamma-irradiated; Sigma) 1 mg/30 g mouse weight by intraperitoneal injection. NMP (1 uL/g mouse weight in PEG, po) was administered 4 hours prior to LPS. Lenalidomide was administered in 2 doses of 100 mg/kg po 24 and 4 hours prior to LPS. Serum was obtained 4 hours after LPS challenge and analyzed for cytokine content by bead array.

For cytokine assessment in MM bearing mice, mice were treated daily for 7d with NMP or SAL, and serum collected 4 hours after the last dose.

Monitoring of Serum Paraproteinemia

Freshly obtained mouse serum was analyzed for paraproteinemia on the Sebia Hydrasys® semi-automated agarose gel electrophoresis system (Sebia, Norcross, Ga., USA). Serum M-spike densitometry quantification was performed using Phoresis software (release 4.7.2, Sebia) by a biochemist blinded to the nature of group allocation. M-spike results are expressed as a percentage of total serum protein.

For correlative quantitative immunoglobulin estimates, thawed aliquots of serum were batched for sandwich enzyme-linked immunosorbent assay (ELISA) using Igλ or IgK capture antibodies (Southern Biotech, AL, USA) and biotin/streptavidin detection by horseradish peroxidase/tetramethylbenzidine dihydrochloride substrate standardized against IgMK/IgMl isotype controls (Biolegend, CA, USA). ELISA plates were read using a VersaMax™ microplate reader and analyzed by SoftMax Pro software v 5.4 (Molecular Devices, CA, USA).

In Vitro Drug Treatment

BEZ235 and lenalidomide were dissolved in dimethylsulfoxide (DMSO) as 10 mM stock solutions and further diluted in media to final concentrations as specified in figure legends. The final concentration of DMSO was not greater than 0.1% v/v in any assay.

Statistical Analysis

One-way Anova was used to compare means of multiple groups; Unpaired T-tests were used to compare means where there were only two groups. Statistical comparisons and Log-rank (Mantel-Cox) survival analyses were calculated using GraphPad Prism version 5.0b at the $\alpha=0.05$ level of significance.

REFERENCES

1. Maira, S. M., et al. Identification and characterization of NVP-BEZ235, a new orally available dual phosphatidylinositol 3-kinase/mammalian target of rapamycin inhibitor with potent in vivo antitumor activity. *Mol Cancer Ther* 7, 1851-1863 (2008).
2. Chesi, M., et al. AID-dependent activation of a MYC transgene induces multiple myeloma in a conditional mouse model of post-germinal center malignancies. *Cancer Cell* 13, 167-180 (2008).
3. Anthony, D. A., et al. A role for granzyme M in TLR4-driven inflammation and endotoxicosis. *J Immunol* 185, 1794-1803 (2010).
4. Yaccoby, S., et al. Antimyeloma efficacy of thalidomide in the SCID-hu model. *Blood* 100, 4162-4168 (2002).
5. Baz, R., et al. Single agent lenalidomide in newly diagnosed multiple myeloma: a retrospective analysis. *Leuk Lymphoma* 51, 1015-1019.
6. Richardson, P., et al. Safety and efficacy of single-agent lenalidomide in patients with relapsed and refractory multiple myeloma. *Blood* 114, 772-778 (2009).
7. Zonder, J. A., et al. Lenalidomide and high-dose dexamethasone compared with dexamethasone as initial therapy for multiple myeloma: a randomized Southwest Oncology Group trial (S0232). *Blood* 116, 5838-5841.

The invention claimed is:

1. A method of treatment of multiple myeloma in a mammalian subject which comprises administering to the subject a composition consisting of an effective amount of N-methyl pyrrolidone (NMP) or a physiologically acceptable salt, solvate or tautomer thereof, as active ingredient.

2. A method of slowing or reducing progression of multiple myeloma in a mammalian subject which comprises administering to the subject a composition consisting of an effective amount of N-methyl pyrrolidone (NMP) or a physiologically acceptable salt, solvate or tautomer-thereof, as active ingredient.

3. The method according to claim 1 wherein the subject is a human.

4. The method according to claim 2 wherein the subject is a human.

5. A method of treatment of multiple myeloma in a mammalian subject which consists of administering to the subject an effective amount of N-methyl pyrrolidone (NMP) or a physiologically acceptable salt, solvate or tautomer thereof, as active ingredient.

* * * * *